United States Patent
Pedersen

(10) Patent No.: US 7,315,626 B2
(45) Date of Patent: Jan. 1, 2008

(54) HEARING AID WITH PERFORMANCE-OPTIMIZED POWER CONSUMPTION FOR VARIABLE CLOCK, SUPPLY VOLTAGE AND DSP PROCESSING PARAMETERS

(75) Inventor: Søren Louis Pedersen, Silkeborg (DK)

(73) Assignee: Microsound A/S (DK)

( * ) Notice: Subject to any disclaimer, the term of this patent is extended or adjusted under 35 U.S.C. 154(b) by 545 days.

(21) Appl. No.: 10/490,303

(22) PCT Filed: Sep. 20, 2002

(86) PCT No.: PCT/DK02/00615

§ 371 (c)(1),
(2), (4) Date: Mar. 19, 2004

(87) PCT Pub. No.: WO03/026348

PCT Pub. Date: Mar. 27, 2003

(65) Prior Publication Data

US 2004/0247148 A1 Dec. 9, 2004

(30) Foreign Application Priority Data

Sep. 21, 2001 (DK) .............................. 2001 01365

(51) Int. Cl.
*H04R 25/00* (2006.01)

(52) U.S. Cl. ...................................... 381/323; 381/312
(58) Field of Classification Search ............... 381/312, 381/315, 320, 323
See application file for complete search history.

(56) References Cited

U.S. PATENT DOCUMENTS

| 4,592,087 | A | * | 5/1986 | Killion ........................ 381/312 |
| 5,569,307 | A | | 10/1996 | Schulman |
| 5,878,146 | A | | 3/1999 | Andersen |
| 6,339,647 | B1 | | 1/2002 | Andersen |
| 6,711,271 | B2 | * | 3/2004 | Hou ............................ 381/312 |

OTHER PUBLICATIONS

International Search Report; PCT/DK02/00615; Jan. 6, 2003.

* cited by examiner

*Primary Examiner*—Suhan Ni
(74) *Attorney, Agent, or Firm*—Cantor Colburn LLP

(57) ABSTRACT

The invention relates to a hearing aid with optimized and controllable power consumption. The power consumption is controlled by varying the voltage level of the supply voltage and/or the frequency of the clock signal. Furthermore the invention relates to a method of optimizing the power consumption of a hearing aid, by calibrating its supply voltage and its clock frequency, and the relation between them, according to the production characteristics of the digital signal processor.

4 Claims, 1 Drawing Sheet

HEARING AID WITH PERFORMANCE-OPTIMIZED POWER CONSUMPTION FOR VARIABLE CLOCK, SUPPLY VOLTAGE AND DSP PROCESSING PARAMETERS

FIELD OF THE INVENTION

The present invention relates to a hearing prosthesis such as a hearing aid or cochlear implant with optimized and controllable power consumption.

BACKGROUND OF THE INVENTION

During recent years, digital hearing aids using fully digital signal processing have advanced on the market due to new and improved properties made possible by advanced digital signal processing algorithms.

The functionality of these digital hearing aids is based on digital signal processing which is typically carried out by a proprietary Digital Signal Processor (DSP) adapted to carrying out one or more signal processing algorithms of the input signals or the input signal from e.g. one or several microphones and/or teleccoils etc. so that an enhanced processed output signal has been optimally adapted to the specific hearing loss of the user.

The used proprietary Digital Signal Processor (DSP) can be a fixed wired type designed to carry out a particular signal processing algorithm or a predetermined selection of such algorithms, or it can be of a programmable type where the predetermined selection of signal processing algorithms are implemented by a computer program or software. In the latter embodiment, the software is at run-time loaded from a non-volatile memory of the hearing prosthesis to a suitable Program RAM storage space and then executed from the Program RAM.

Irrespective of the type, the DSP requires the processing of the algorithm to be controlled by a clock signal which, in turn, will typically be derived from a master clock generator. The clock signal furnished to a contemporary DSP typically has a frequency between 1-4 MHz. Since the power consumption of a digital CMOS circuits, among others, is proportional to the clock frequency by which it is controlled, it is desirable to, on the one hand, keep the clock frequency as low as possible to save power/effect while on the other hand, it is desirable to make the clock frequency as high as possible in order to support more advanced signal processing algorithms, such as noise reduction and adaptive feedback suppression etc.

Thus, there exists a need in the art for a DSP-based hearing aid, in which the actual clock frequency of the DSP processor is dynamically and adaptively adjustable.

SUMMARY OF THE INVENTION

The present invention relates to a hearing aid comprising digital signal processor means (DSPM), power supply means (PSM), clock generator means (CGM), power consumption control means (PCCM); said digital signal processor means being provided with at least one input signal (IS) to generate at least one output signal (OS), said digital signal processor means being supplied with voltage by said power supply means, and said digital signal processor means being driven by a clock signal deriving from said clock generator means; said power consumption control means being adapted for controlling the power consumption of said digital signal processor means during operation of the hearing aid.

According to the invention, an advantageous embodiment of a hearing prosthesis with low average power consumption has hereby been obtained. The reduced power consumption results in many advantageous effects, as e.g. increased battery lifetime, the possibility of using smaller batteries etc., which in turn may result in, among other things, the possibility of building smaller and more aesthetic looking hearing aids, and additionally lowering battery costs for the user.

A hearing prosthesis according to one embodiment of the present invention furthermore makes it possible to use a significantly higher clock signal frequency for the DSPM in at least some time periods of the operation time of the hearing prosthesis. The higher clock frequency makes it possible for the DSPM to execute complex signal processing algorithms, such as noise reduction or parametric based signal modeling, which can not be supported by the nominal clock frequency when the user is situated in particularly adverse or difficult listening environments.

According to the invention, digital signal processor means may refer to one or more Digital Signal Processors DSP, one or more microprocessors, one or more logic circuits or any other means for digital signal processing. Clock generator means may refer to any means for generating a clock signal suitable for driving the digital signal processing means, as e.g. a crystal oscillator, a ring oscillator, a RC based oscillator or any other clock oscillator. The clock signal generated may preferably be a square wave signal, but any other signal suitable may be used. The clock signal may be refined by subsequent circuits as e.g. a phase locked loop PLL, a clock shape enhancing circuit, etc. Power supply means may refer to any suitable power supply, e.g. batteries. A preferred embodiment of the invention uses a Zinc-air battery, which is not rechargeable, or a Lithium-Ion battery, which is rechargeable. Other usable battery types comprise mercuryoxide, silver-oxide, nickel-cadmium NiCD, nickel-metalhydride NiMH or lithium Li batteries.

Finally, it is noted that the hearing prosthesis may comprise additional electronic circuitry which is well-known in the art such as A/D, converters, preamplifiers, voltage regulators etc. not specifically mentioned here.

In a preferred embodiment of the invention, the said power consumption control means (PCCM) comprise means for varying the frequency of said clock signal supplied to at least a part of the DSPM.

According to this embodiment, varying the frequency of the clock signal that drives the digital signal processor means controls the power consumption of the digital signal processor. As the power consumption of e.g. a CMOS digital circuit is approximately proportional to the frequency of the clock signal, it is possible to control the power consumption by varying the clock frequency. A preferred range of frequencies to vary between, comprise the frequency range 1 MHz-20 MHz, and an even more preferred range comprise 1 MHz-8 MHz.

In a preferred embodiment of the invention, said power consumption control means (PCCM) comprise means for varying said frequency in proportion to a nominal value.

According to this embodiment, a nominal frequency value may be predefined during the manufacturing of the hearing prosthesis. This nominal value may then be used when no specific frequency is selected, i.e. default.

In a preferred embodiment of the invention, the said nominal value is selected from the lower end of the possible frequency range.

According to this embodiment, the clock generating means may generate a clock signal with a proportionally low frequency, as e.g. 1 MHz. The power consumption control means may then, when the digital signal processor means needs a higher clock frequency, establish such a clock signal by multiplying the frequency of the clock signal generated by the clock generator means.

In a preferred embodiment of the invention, the said means for varying the frequency of said clock signal comprise means for multiplying the frequency.

According to this embodiment, the nominal frequency may be multiplied to support more advanced use of the digital signal processor means. Possible means for multiplying the frequency comprises among others controllable analogue or digital phase locked loops PLL.

In an alternative preferred embodiment of the invention, the said nominal value is selected from the higher end of the possible frequency range.

According to this embodiment, the clock generator means may generate a clock signal with a proportionally high frequency, as e.g. 8 MHz. The power consumption control means may then, when the digital signal processor means makes use of less demanding algorithms, provide a clock signal with a lower frequency to the DSPM by dividing the frequency of the clock signal generated by the clock generator means.

In an alternative preferred embodiment of the invention, the said means for varying the frequency of said clock signal comprise means for dividing the frequency.

According to this embodiment, the nominal frequency may be divided when the digital signal processor means used in a less advanced way. Possible means for dividing the frequency comprises among others controllable or programmable division circuits.

In yet an alternative preferred embodiment of the invention, the said power consumption control means (PCCM) comprise means for varying the voltage level of said power supply means. This embodiment may be used together with the first preferred embodiment, as to let the power consumption control means comprise both means for frequency and voltage adjustments.

Preferably, before the clock frequency of the DSPM is adjusted up or down relative to the current clock frequency, the voltage level of the power supply means is detected. The voltage level may be detected through a PCMM readable A/D converter which is connected to the power supply means. The PCCM will e.g. determine whether the intended clock frequency is supported by the existing supply voltage or a new and higher supply voltage level is required in order allow the DSPM to operate on the intended clock frequency.

This decision may advantageously be based on pre-stored calibration information describing clock frequency versus supply voltage characteristics of the DSPM of the hearing prosthesis as described in more detail below. A set of predetermined rules is applied by the PCMM to determine a new optimal voltage level of the power supply means for the intended or target clock frequency.

If the target clock frequency is significantly higher than the present clock frequency and therefore can not be supported on the previously determined voltage level of the power supply means, its voltage level is increased to a new and higher value that has been determined by the PCMM as the approximate minimum value required for the target clock frequency in question.

On the other hand, if the target clock frequency is lower than the present clock frequency, it is known that the current voltage level of the power supply means also is able to support the new clock frequency. In this situation, it will often be possible to lower the voltage level of the DSPM and therefore, the PCMM preferably determines and sets a new and lower voltage level for the power supply means. This methodology accordingly ensures that the operation voltage of the DSPM is kept at a substantially minimum value for the selected clock frequency and ensures that the power consumption of the DSPM is minimized.

According to this embodiment, by varying the voltage level supplied to at least part of the DSPM, it is possible to control the power consumption of the DSPM, as the power consumption of e.g. a CMOS digital circuit is approximately proportional to the square of the supply voltage. A preferred range of voltage levels to vary between, comprise the range 0.5 V-1.1 V, and even more preferred are the sub ranges 0.7 V-1.0 V. This range of voltage levels can be provided by means of a step-down DC-DC converter often called a buck-converter connected to the battery supply of the hearing prosthesis. By e.g. lowering the supply voltage to the DSPM from 1.3 V to 1.0 V, the power consumption of the digital signal means is lowered by approximately 60-70%. The voltage level supplied to the DSPM may also be higher than the battery voltage such between 0.1-0.5 Volt higher than the current battery voltage of the hearing prosthesis. This may be obtained by the use of voltage multiplier connected to the battery voltage.

In an alternative preferred embodiment of the invention, the said power consumption control means (PCCM) comprise means for varying said voltage level in proportion to a nominal voltage level.

According to this embodiment, a nominal voltage level may be predefined. This nominal value may then be used as a default immediately after boot of the DSPM. It may be beneficial to only vary the supply voltage to part of the electronic circuit, e.g. a DSP core part of the digital signal processor means comprising the multiply-accumulator MAC and the RAM circuits.

In an alternative preferred embodiment of the invention, the said nominal voltage level being selected from the lower end of the possible voltage range.

According to this embodiment, the power supply means may provide a supply voltage with a proportionally low level. This nominal value may be selected to equal the voltage level the used type of battery reaches at the end of its lifetime. E.g. when using a Zinc-air battery type, the nominal voltage level may be set to 1.0 V. The power consumption control means may then, when the digital signal processor means or part of the digital signal processor means needs a higher voltage level, establish such a voltage level by increasing the voltage.

According to this embodiment, the voltage level of the power supply means may be increased relative to the nominal voltage level to support more advanced use of the digital signal processor means such as executing complex signal processing algorithms. Possible means for controlling the voltage level comprises a DC-DC converter, based on e.g. switch-mode technique.

In a yet alternative embodiment of the invention, the said power consumption control means (PCCM) comprise means for monitoring at least one of said at least one input signal (IS) and said at least one output signal (OS) and means for determining a frequency and voltage level on the basis thereof.

According to this embodiment, the power consumption control means may continuously determine the frequency and/or voltage level to use on the basis of characteristics of the input signal and/or the output signal. Such characteristics may comprise e.g. signal/noise ratio, amplitude, etc. As indicated, this embodiment may be used together with any of the previously described embodiments.

In an alternative preferred embodiment of the invention, the said power consumption control means (PCCM) comprise means for at least partly determining a clock frequency and voltage level of the DSPM on the basis of the signal processing algorithms currently active in the digital signal processor means (DSPM).

According to this embodiment, the power consumption control means may continuously determine the clock frequency and/or voltage level to use on the basis of the current use of the digital signal processor means. E.g. when the digital signal processor means is in use to its full capacity, it may be necessary to increase the voltage level to a maximum value, and e.g. when the digital signal processor means runs or executes an algorithm with multiple operations per input data sample, it may be necessary to raise the clock frequency. Accordingly the voltage level and/or the clock frequency may be lowered as soon as the need for extra computational power expires. Thus it may be possible to achieve a very low average power consumption of a hearing prosthesis in accordance with the present invention compared to prior art hearing aids.

In an alternative preferred embodiment of the invention, the said power consumption control means (PCCM) comprise means for at least partly determining a frequency and voltage level on the basis of a users choice of a specific program among a set if user selectable listening programs.

According to this embodiment, the hearing aid may be of a multiple program type, having means, e.g. a switch, for letting the user choose a specific signal processing program or listening program from a selection of predefined signal processing programs. When using such a hearing aid, the power consumption control means may determine the voltage level and frequency best suited to be used with the currently chosen program. Alternatively a voltage level and a frequency for each selectable program may be predefined in the power consumption control means.

In a yet alternative preferred embodiment of the invention, the said power consumption control means (PCCM) is at least partially comprised by said digital signal processor means (DSPM).

According to this embodiment, some elements of the power consumption control means (PCCM) may be implemented as program routines within the digital signal processor means (DSPM). Such elements may e.g. comprise means for monitoring input and output signals of the hearing prosthesis and means for determining an optimal voltage level and clock frequency for the DSPM on the basis thereof, or on the basis of the active signal processing algorithm. Other parts of the power consumption control means may be comprised by the digital signal processor means as well. This embodiment may be used together with any of the previously described embodiments.

In another embodiment of the invention, the clock frequency versus supply voltage characteristics of the DSP has been determined during manufacturing of the hearing prosthesis or fabrication of the DSPM. Calibration information representing that property has been recorded in a non-volatile memory device of the hearing prosthesis. This calibration information is read and used by the DSP to determined an optimum supply voltage of the DSPM at a chosen clock frequency. The setting of the clock frequency may be selected in an adaptive manner in response to the current processing load on the DSPM. This processing load will for example depend on which listening program that the user has chosen. In a yet alternative preferred embodiment of the invention, the said electronic circuitry (EC) comprise non-volatile or permanent memory means (PMM) for recording information on voltage level, frequency and signal processing algorithm; and means for utilizing said recorded information adaptively, to continuously optimize the functionality of said power consumption control means (PCCM).

According to this embodiment, the power consumption control means may continuously base its adjustments on records of preceding settings. Thereby the power consumption control means possibly becomes more and more able to control voltage level and clock frequency in the most optimal way. Additionally, when some characteristics possibly changes over time during use, it may be possible for the power consumption control means to keep track of it, and always be able to make optimized adjustments. This embodiment may be used together with any of the previously described embodiments.

In a yet alternative preferred embodiment of the invention, the said electronic circuitry (EC) comprise means for enabling or disabling functionalities of said digital signal processor means (DSPM) in accordance with the type and condition of said power supply means (PSM).

According to this embodiment, it may be possible to use different power supply means, e.g. battery types, to enable the user to choose e.g. heavy processing algorithms by fitting a battery with higher voltage, or choose simpler processing algorithms in return for cheaper batteries or a lighter hearing aid. This embodiment may be used with any of the previously described embodiments of the invention.

Another aspect of the present invention relates to a method of controlling power consumption of a hearing aid comprising electronic circuitry (EC), comprising the steps of supplying voltage to a digital signal processor means (DSPM) from a supply voltage established by power supply means (PSM); driving said digital signal processor means using a clock signal derived from clock generator means (CGM); varying at least one characteristics of said electronic circuitry by means of power consumption control means (PCCM).

According to the invention, an advantageous method of lowering the average power consumption of a hearing aid has hereby been obtained. The terms electronic circuitry and power consumption control means refer to the above description.

The reduced power consumption may result in many advantageous direct effects, as e.g. extension of a battery's lifetime, the possibility of using smaller batteries, less heat generation, etc., which in turn may result in, among other things, the possibility of building smaller and more aesthetic looking hearing aids, and additionally being still cheaper to supply with batteries.

In a preferred embodiment of the invention, the said at least one characteristics comprise the frequency of said clock signal.

According to this embodiment, a preferred range of clock frequencies to vary between comprises the range 1 MHz-20 MHz, and an even more preferred range is 1 MHz-8 MHz. This range highly depends on the digital signal processor means used, and the complexity and extensity of processing algorithms imaginable.

In an alternative preferred embodiment of the invention, the said at least one characteristics comprises the voltage level of said supply voltage.

According to this embodiment, a preferred range of voltage levels to vary between comprises the range 0.7 V-1.3 V. Very preferred sub ranges comprises the ranges 1.0 V-1.3

V and 0.7 V-1.1 V. These ranges highly depend on the type of battery used. This embodiment may be used together with the previously described embodiment.

In a preferred embodiment of the invention, the said frequency of said clock signal is adjusted by a user.

According to this embodiment, the user may control the clock frequency in accordance with the present sound environment.

In a preferred embodiment of the invention, the said frequency of said clock signal is continuously adjusted according to the present requirements of said digital signal processor means (DSPM).

According to this embodiment, the clock frequency may be adjusted according to the number of operations needed to be performed between each data sample with the present signal processing algorithm.

In a preferred embodiment of the invention, the said frequency of said clock signal is continuously adjusted according to the signal/noise ratio of a present input signal (IS).

According to this embodiment, the clock frequency may be determined from the quality of the input signal, as it in turn determines the processing algorithm to be used in the digital signal processing means.

In a preferred embodiment of the invention, the said power supply means (PSM) is a battery, and said frequency of said clock signal is continuously adjusted according to the voltage level of said battery.

According to this embodiment the power supply means may choose a lower frequency when the battery is about to be exhausted, to let it last as long as possible.

In a preferred embodiment of the invention, the said frequency of said clock signal is adjusted according to said users present selection of hearing aid program among several selectable predefined hearing aid programs.

According to this embodiment, a hearing aid may be pre-programmed with different user-selectable sound processing programs according to different sound environments. As these programs may have different requirements to the clock signal frequency, it may be beneficial to predefine the frequencies to use with each of these programs, and hence automatically change the frequency when the user selects a new program.

In a preferred embodiment of the invention, the said voltage level of said power supply means (PSM) is adjusted according to the present requirements of the digital signal processor means (DSPM).

According to this embodiment, it may be beneficial to only supply the voltage level that is necessary in a certain signal processing situation. When e.g. very little signal processing is performed, only a small part of the digital signal processing means is used, and it does not require the same voltage level as when the full digital signal processing means is in use due to heavy processing needs.

In a preferred embodiment of the invention, the said voltage level of said power supply means (PSM) is adjusted according to said users present selection of hearing aid program among several selectable predefined hearing aid programs.

According to this embodiment, a hearing aid may be pre-programmed with different user-selectable sound processing programs according to different sound environments. As these programs may have different requirements to the digital signal processor means, and it in turn have different requirements to the supply voltage, it may be beneficial to predefine voltage levels to use with each of these programs, and hence automatically change the supply voltage when the user selects a new program.

In a preferred embodiment of the invention, the information of said adjustments made to said voltage level and said clock frequency is recorded and stored in permanent memory means (PMM), and said information is processed and used for optimizing the adjustments of said voltage level and clock frequency.

According to this embodiment, it may be very beneficial to keep track of the adjustments and combination made, to utilize this information for optimizing later adjustments.

According to this embodiment, the processing and utilization of stored data may be performed adaptively during use, or technicians may carry it out at intervals, to manually optimize that hearing aid or later models.

In a preferred embodiment of the invention, the said digital signal processor means (DSPM) comprises functionalities selectable by changing said power supply means (PSM).

According to this embodiment, a hearing aid may comprise advanced processing algorithms so computationally demanding, that they may only be enabled by supplying a voltage higher than the battery voltage to the DSPM from the power supply means.

Since there may be considerably differences between the maximum clock frequency on which a particular DSP device can sustain error-free operation at a given supply voltage, it is advantageous to determine clock frequency versus supply voltage characteristics of the particular DSP device or a batch of DSP devices to which the particular DSP device belongs.

After the clock frequency versus supply voltage characteristics of the DSP has been determined, calibration information representing that property may be recorded in a non-volatile memory device of the hearing prosthesis that houses the DSP device or directly into a non-volatile memory area of the DSP device itself.

The power consumption control means are adapted to read the calibration information from the non-volatile memory during boot or initialization of the DSPM in the hearing prosthesis. The power consumption control means subsequently uses the calibration information to determine the minimum supply voltage on which the DSPM can operate and to adjust the voltage level of the PSM to the minimum supply voltage.

Alternatively, in case that the hearing prosthesis does not comprise a PSM with an ability to adjust the voltage level during operation of the hearing prosthesis, the voltage level of the PSM can be set to a fixed value during the manufacturing process of the hearing prosthesis in accordance with the determined calibration data for the DSP in question or calibration data for the batch of DSPs. Since the maximum clock frequency on which it is required to operate the DSPM is known at the time of manufacture, it is secured that all hearing prostheses uses a supply voltage level for their respective DSPM that is as small as possible and as such minimizes the power consumption of the DSPM in each individual hearing prosthesis.

According to this embodiment, it may be beneficial to establish a curve showing the maximum clock frequency in proportion to the voltage level. This relationship may be one of the characteristics that differ between different production batches.

In a preferred embodiment of the invention, the said calibration data is stored by means of permanent memory (PMM) in the hearing prosthesis.

According to this invention, the calibration data may be stored in permanent memory, as e.g. flash-ROM, EEPROM, etc, to ensure they are not erased or altered. This permanent memory may be readable from the digital signal processor means (DSPM) or a special circuit controlling the voltage level and frequency.

In a preferred embodiment of the invention, the said digital signal processor means (DSPM) or said power consumption control means (PCCM) upon startup reads and utilizes said calibration information.

According to this embodiment, the calibration data may read and automatically used for calibration, when the hearing aid is switched on.

BRIEF DESCRIPTION OF THE DRAWING

The invention will now be described in detail with reference to a drawing, in which.

DETAILED DESCRIPTION

Figure 1:
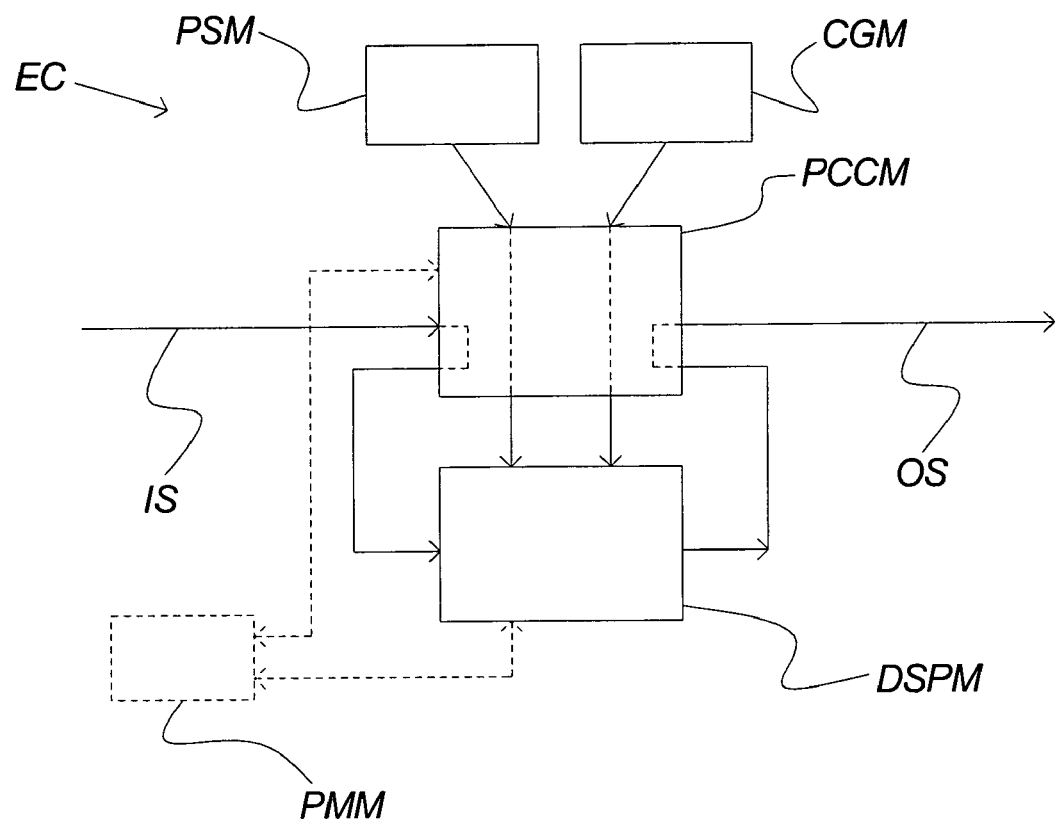
FIG. 1 shows a preferred embodiment of the invention.

FIG. 1 shows a block diagram of the present invention. It illustrates an electronic circuitry EC comprising digital signal processing means DSPM, power supply means PSM, clock generator means CGM and power consumption control means PCCM.

The digital signal processor means DSPM may be a programmable digital signal processor DSP, a programmable gate array PGA or similar, fixed-wired logic circuits, a microprocessor or any other means capable of processing signals. Preferably a programmable digital signal processor is used.

The power supply means PSM preferably comprises a battery, preferably of the Zinc-air type. The clock generating means CGM may be any clock generator able to establish a clock signal suitable for the digital signal processor means DSPM applied. The clock generating means CGM may comprise any additional circuits necessary to refine the clock to a usable quality.

The power consumption control means PCCM is able to adjust e.g. the voltage level supplied to the rest of the circuit or part of it, or the frequency of the clock signal fed to the digital signal processor means DSPM. What functionalities the power consumption control means comprises, depends on the set-up and the range of control wanted. Detailed examples of different possible sub-circuits inside the power consumption control means are given below.

In addition to the above described blocks, the electronic circuitry EC comprises an input signal IS and an output signal OS. The input signal may be provided by one or more acoustical or magnetic transducers analog-to-digital converters. The input signal is fed to the digital signal processor means DSPM, possibly through the power consumption control means PCCM, thereby making it possible for the power consumption control means to base some of its adjustments on predetermined characteristics of the input signal IS. The output signal OS is an output from the digital signal processor means DSPM. It may be sent to one or more acoustical transducers or electric transducers through a digital-to-analog converter.

Furthermore the electronic circuitry may comprise permanent memory means PMM. It may be Flash-ROM, EEPROM, RAM with a battery back-up or any other kind of memory suitable to hold information while the hearing aid is switched off. This memory may according to the present invention be used to hold information of e.g. the calibration data of the digital signal processor means DSPM or records of past adjustments made by the power consumption control means PCCM. The permanent memory means PMM is not a necessary part of the invention, though it is part of the preferred embodiment.

With a preferred embodiment of the present invention, the clock frequency is altered during normal use of the hearing aid, with the distinct possibility of increasing it from the predetermined value determined during production. In a preferred embodiment, the predetermined nominal clock frequency of the processor is 2 MHz while the dynamic clock frequency may be increased to e.g. 3, 4 or 8 MHz. The decision to increase the clock frequency or to reduce it again may be carried out by a monitor circuit designed for this purpose.

According to a preferred embodiment, the monitor circuit automatically analyzes characteristics of the input signal or input signals IS and determines that once one or several predetermined conditions have been met, the clock frequency of the DSP processor DSPM is increased or lowered to a predetermined value or with a predetermined ratio such as +50%, +100%, +150% or −50% etc. For example, such a monitor circuit may be adapted to analyze the signal noise ratio of one or more input signals, and once this ratio falls below a predetermined threshold value, e.g. +5 dB, +2 dB, 0 dB or −2 dB (over a selected bandwidth), the clock frequency of the DSP is increased to the predetermined value so that it is capable of supporting a complex noise reduction algorithm entered from an associated, permanent memory or activated from a certain address in e.g. a program RAM. Said noise reduction algorithm may e.g. be based on spectral subtraction and/or spatial filtration or beam forming, of microphone signals provided by a pair of closely-spaced microphones mounted in the same hearing aid.

In a second embodiment, the user chooses when and for how long the device should be in a state of increased clock frequency. The activation itself may e.g. take place by a spoken command from the user, by remote or manual activation of a switch, typically the program switch already available in many digital hearing aids. In such a multi-program hearing aid, it is possible to have one or more of the provided program selections associated with use in certain, typically problematic, listening or sound environments requiring more complex sound processing than the one taking place with the default program selection of the hearing aid.

Despite the fact that the increased power consumption, which inevitably follows from the use of the increased clock frequency, may be unacceptable if it is a constant or almost constant phenomenon, such increased power consumption may be fully acceptable for short time periods during which the user of the hearing aid is in a adverse sound environment, such as a train station or a noisy restaurant/cafe, or an acoustically poor conference room with a lot of reverberation and/or a lot of simultaneously talking individuals etc. Thus, it may be fully acceptable to a lot of hearing aid users to have their hearing aid use several times the normal amount of power under such adverse conditions if the hearing aid is able to provide a significant improvement in the user's ability to communicate under such adverse conditions. It would, of course, be particularly acceptable if the adjustment with the increased clock frequency were only to be applied for brief periods of time in relation to the entire utilization period of the device since the average power consumption of the hearing prosthesis would thereby only be marginally increased. For example, it is entirely possible to have the activation of the adjustment of increased clock frequency take place only by 5 to 10 or max. 30 percent on a normal day while the average state would be active for the remaining time.

The clock frequency of the DSP itself may be controlled by an analogue or digitally-controlled circuit, e.g. a phase locked loop PLL, in which various clock multiplication factors of the system have been made controllable via a dedicated register which, in turn, may be written or read from the DSP. In this embodiment of the invention, the master clock generator CGM may run at a constant clock frequency which may be lower than the desired regulation span of the clock frequency of the DSP itself, while the DSP is being driven by said programmable control PLL-based multiplication circuit. This circuit may e.g. comprise integral division factors between 1 and 8 or between 1 and 16. In an alternative embodiment, the master clock generator CGM operates at a constant clock frequency with a frequency which is higher than the desired regulation span of the clock frequency of the DSP itself, while the clock frequency of the DSP itself is generated by a controllable division circuit.

In an automated embodiment of the invention, the PLL may be controlled by said monitor circuit and this monitor circuit may be incorporated in the DSP or be designed as a program routine of the software of the DSP.

It is important to note that if only the clock frequency of the DSP is changed, while the sampling frequencies of A/D and D/A converters and other data rates of other I/O units in the system are maintained, it may be necessary to provide a corresponding change of the timing in these units to maintain correct timing of the data signals between the I/O units and the DSP.

Another aspect of the invention relates to the possibility of providing a DSP-based hearing aid in which the relevant supply voltage for a part or all of the DSP is dynamically adjustable, i.e. during use of the hearing aid. According to this embodiment, the supply voltage of the DSP may either be increased or lowered from the preset value which may e.g. be determined at the time of production. Since the power consumption of digital CMOS circuits is basically proportional to the square of the supplied supply voltage, it is advantageous to provide the DSP with the lowest possible voltage which, at the same time, allows the DSP to support the algorithm(s) currently being executed on the DSP. Thus, if the DSP is to execute algorithms of varying calculation intensity depending on e.g. the surrounding sound environment, the supply voltage has traditionally been preset to a fixed value so that the most calculation-requiring algorithm could be supported (worst case condition). This is unfortunate in the sense that during the times at which the most calculation-requiring algorithms are not executed on the DSP, it operates with a supply voltage which is higher than required, whereby the effect consumption of the entire hearing aid is significantly increased.

It will especially be particularly advantageous to provide supply voltage to the core part of the DSP, comprising MAC and RAM circuits, with an energy-efficient DC-DC converter, e.g. based on switch mode technique and attached to the battery supply of the hearing aid. This battery supply will typically be based on a Zinc-air battery with a nominal voltage of approx. 1,30 V when the battery is new. The output voltage from said DC-DC converter may advantageously be adjusted to approx. 1,0 V, e.g. at the time of production, which is the minimum voltage to be held by the battery at the end of its useable lifespan anyway. By providing the core part of the DSP with a 1,0 V voltage instead of a 1,3 V, the power consumption of the DSP core will be lowered by approx. 60 to 70%. The DC-DC converter may be based on anyone of several well-known conversion principles and make use of a switched capacitor or LC principles, by which the output voltage from the DC/DC-converter is adjusted to the desired reference value via a feedback loop. The switching frequency may advantageously be placed in the range between 200 kHz and 2 MHz. According to a preferred embodiment, the output voltage of the DC-DC converter is dynamically adjustable and may e.g. be controlled automatically by a monitor circuit monitoring which algorithms is currently active in the hearing aid and choose the lowest output voltage of the DC-DC converter on the basis of such information, which may make the DSP capable of supporting the active algorithms by being capable of operating errorless at the necessary clock frequency.

The maximum clock frequency, at which the DSP is capable of operation, is strongly dependent of the supply voltage to the core part of the DSP and, thus, there is a limit as to how low or high the value can be adjusted in terms of the supply voltage. However, by dynamically adjusting the supply voltage in dependency of the chosen clock frequency, a significant power saving on the battery consumption may be obtained during the period of time in which only the slightly calculation-requiring algorithms are active and it is only necessary to clock the DSP at a relatively low frequency. Thus, it is sufficient to increase the supply voltage during the periods of time in which the more or less complex or calculation-requiring algorithms are active and at the same time increase the clock frequency of the DSP itself.

For example, the supply voltage to the core part of the DSP may be adjusted to a predetermined value e.g. 1,0 V or 0,9 V during production of the hearing aid, which allows the DSP to operate at the determined nominal clock frequency of e.g. 2 MHz. Thus, the default algorithms incorporated in the hearing aid may be executed at these conditions and the hearing aid may be able to start up without any problems. If it should turn out during subsequent operation of the device to be necessary to increase the clock frequency to a higher value, e.g. the previously mentioned 4 MHz, the monitor circuit may at the same time program the supply voltage to the core part of the DSP to an increased value from the initial 1,0 V to e.g. 1,1 V. On the other hand, it may also be possible to correspondingly adjust the clock frequency dynamically to a lower value, e.g. 1 MHz, if the hearing aid is in an "uncomplicated" sound situation or sound environment. At the increased supply voltage, the DSP may thus be capable of operating faster (at the expense of the effect consumption) while the lower supply voltage may make the DSP slower but reduce power consumption significantly. Furthermore, it may be possible to increase the output voltage of the DC-DC converter to exceed that of the current battery voltage by an appropriate design of the DC-DC converter. Despite the fact that this will result in increased effect consumption, it may also lead to the possibility of operating the DSP core at a very high clock frequency and thereby support very calculation-requiring algorithms. In this context, it is worth mentioning that today's most advanced commercial DSP circuits from companies like Motorola, Texas Instruments, Analog Devices etc. are already capable of operating at their respective maximum clock frequencies at supply voltages ranging in the area of 1,5 to 1,8 volts. The required supply voltage to be applied in order to achieve maximum speed will furthermore be further decreased in future DSP generations due to the constantly decreasing geometrical dimensions of CMOS technologies.

In a preferred embodiment of the invention, the output voltage from the DC-DC converter is made dynamically adjustable or programmable in the range between 0,7 and 1,1 volt in steps of 50 mV. However, the invention is not limited to this as it is also possible to choose a battery with a higher voltage than the commonly used (e.g. a rechargeable) so that the device may feature different performances depending on the battery type.

A further alternative embodiment of the invention concerns the possibility of individual adjustment or programming of the output voltage from the DC-DC converter so that it is optimally adjusted to the relevant process dependent minimum operational voltage of the DSP. Since production of integrated circuits is a batch process, this means that almost all circuits in a given batch basically have similar characteristics in terms of cohesion between the supplied supply voltage and the maximum clock frequency at which the DSP may operate. However, the result of the wafer fabrication process of individual batches may vary considerably. Thus, it may be an advantageous improvement to provide a hearing aid with an associated permanent memory PMM, e.g. flash or EEPROM, in which calibration information characterizing the individual DSP requirements to supply voltage vs. maximum clock frequency is been stored. According to this embodiment of the invention, the DSP may boot in a standard mode in terms of clock frequency and supply voltage which takes into consideration the worst-case process outcome in such a manner that operation of the DSP is always ensured. A program routine in the DSP subsequently reads said stored calibration information and uses it to determine how the supply voltage of the DSP of the hearing prosthesis should be lowered and still operate at the contemplated clock frequency. Finally, the supply voltage of an adjustable or programmable DC-DC converter is set to the previously determined minimum value. Accordingly the power consumption of the DSP can be reduced to an absolute minimum level based on individually or batch related process outcome.

If this embodiment of the invention is applied together with the possibility of varying the clock frequency of the DSP as previously described, it is also possible to determine the calibration information concerning the minimum applicable supply voltage over a sufficient span of clock frequencies. For example, minimum values for supply voltages according to clock frequencies in a range from e.g. 1 to 20 MHz, or more preferable 1 to 10 MHz, may be determined. In this manner, it is possible to adjust the supply voltage of the DSP in such a manner that the DSP is always operating at the lowest possible supply voltage at any given clock frequency.

The invention claimed is:

1. A hearing aid, comprising:
   digital signal processor means;
   power supply means;
   clock generator means;
   power consumption control means;
   said digital signal processor means being provided with at least one input signal to generate at least one output signal;
   said digital signal processor means being supplied with voltage by said power supply means; and
   said digital signal processor means being driven by a clock signal deriving from said clock generator means; and
   said power consumption control means being adapted for controlling power consumption of said digital signal processor means during operation of the hearing aid;
   wherein said power consumption control means is configured to vary at least one of a frequency of said clock signal and a voltage level of said power supply means.

2. A hearing aid according to claim 1, wherein said power consumption control means comprise means for varying a frequency of said clock signal and means for varying a voltage level of said power supply means.

3. A method of controlling power consumption of a hearing aid during operation, comprising electronic circuitry, comprising:
   supplying voltage to a digital signal processor means from a supply voltage established by power supply means;
   driving said digital signal processor means using a clock signal derived from clock generator means; and
   varying at least one characteristic of said digital signal processor means by power consumption control means;
   wherein said at least one characteristic is selected from a frequency of said clock signal and a voltage level of said supply voltage.

4. A method of controlling power consumption of a hearing aid according to claim 1, wherein information of adjustments made to said voltage level and said clock frequency is recorded and stored in permanent memory means, and said information is processed and used for optimizing the adjustments of said voltage level and clock frequency.

* * * * *